United States Patent [19]
Cowell et al.

[11] 3,932,756
[45] Jan. 13, 1976

[54] X-RAY DETECTOR FOR A PANORAMIC X-RAY DEVICE

[75] Inventors: David Cowell, Webster; Frieder H. Ensslin, Rochester, both of N.Y.

[73] Assignee: Sybron Corporation, Rochester, N.Y.

[22] Filed: June 24, 1974

[21] Appl. No.: 477,897

[52] U.S. Cl. .............. 250/361; 250/320; 250/370
[51] Int. Cl.² ........................................... G01T 1/20
[58] Field of Search .......... 250/313, 320, 322, 361, 250/362, 370, 371, 458, 459, 460, 475, 476

[56] References Cited
UNITED STATES PATENTS

| | | | |
|---|---|---|---|
| 3,119,016 | 1/1964 | Attix | 250/370 |
| 3,669,544 | 6/1972 | Heller | 250/313 X |
| 3,743,835 | 7/1973 | Koncen | 250/370 X |
| R26,497 | 12/1968 | Splain | 250/322 |

*Primary Examiner*—Archie R. Borchelt
*Attorney, Agent, or Firm*—Theodore B. Roessel; J. Stephen Yeo

[57] ABSTRACT

An X-ray detector for converting X-ray energy into electrical energy which contains a X-ray sensitive fluorescent screen optically coupled to a photovoltaic energy conversion cell. An electrostatic shield is provided at the input of said fluorescent screen to shield the detector from both background electrical noise and ambient light. Mechanical configurations and electrical flexibility make the detector particularly well suited for the control of panoramic X-ray machines.

6 Claims, 5 Drawing Figures

X-RAY DETECTOR FOR A PANORAMIC X-RAY DEVICE

BACKGROUND OF THE INVENTION

This invention relates generally to X-ray detectors and more particularly concerns X-ray detectors for the control of panoramic X-ray machines.

X-ray detectors known and used in the prior art are subject to deficiences. Previous X-ray detectors have been bulky, expensive and prone to instability and parametric drift. These detectors include a fluorescent screen which upon excitation by X-rays emit light which is directed to a photo sensitive electronic tube. Electrical characteristics of the tube are such as to require a high impedance load, as well as requiring external high voltage power supplies. Photo-electric tubes are relatively bulky and are fixed in shape. The sensitive area of the tube is only a small portion of the body of the tube. Some applications require that an X-ray detector meet certain geometric configurations. The use of photosensitive vacuum tubes preclude the flexibility required by these applications.

One such application is a panoramic X-ray machine. A panoramic X-ray machine is used to take full mouth X-rays in one continuous operation. This is accomplished by providing a X-ray source on one side of the patient's skull and arranged diagonally opposite of the patient's skull, a film cassette or holder for transporting a filmstrip for recording X-ray images obtained thereby. The X-ray source and the film cassette rotate about the patient's skull in a predetermined path maintaining an area of the patient's teeth in the focal plane of interest. When the front teeth are being X-rayed, the X-ray source must be positioned behind the patient's neck while the film cassette is located in the proximity with the patient's lips. When side teeth are being X-rayed, the X-ray source on one side of the patient's face, while the cassette is on the other. While X-raying through the patient's neck, the X-ray beam must pass through the skull, vertibra and other X-ray absorbing tissue. Conversely, when X-raying teeth on the side of the patient, the X-ray encounters appreciably less attenuation. X-ray film has very limited range of exposure latitude. Thus, without compensation, a given panoramic X-ray might be overexposed as to the side teeth, but underexposed as to the front teeth. For this reason, it would be desirable for an X-ray detector to be mounted in proximity to the film cassette for providing a signal corresponding to the amount of X-rays passing through the skull. The signal may be used to amplitude modulate the X-ray source or to control the speed of rotation of the X-ray source and the film cassette. The X-ray beam passing through the skull is typically 4 or 6 inches in height and one-eighth or one-fourth inches wide at the image receptor area where detection must take place. It would, therefore, be highly desirable to provide a detector that met this geometric configuration while being devoid of external power supply or unnecessary bulk. Since devices such as the panoramic X-ray are often intended for commercial use, economy is also an important consideration.

SUMMARY OF THE INVENTION

An X-ray detector has an electrical output signal that corresponds to a detected X-ray signal. The detector is comprised of a fluorescent screen which emits light in response to X-rays and at least one semiconductor photovoltaic energy conversion cell arranged in optical communication with the fluorescent screen for generating an electrical output in response to light emitted by the fluorescent screen. The photovoltaic energy conversion cell and the fluorescent screen are chosen to have matching spectral characteristics so that the visible light emitted by said fluorescent screen is optimumly converted by said photovoltaic cell. A feature of the invention, is that a electrostatic shield of metallic foil is arranged across the receiving side of said fluorescent screen for protection of the X-ray detector from un-wanted electrical signals and ambient light. In some applications, the X-ray source may produce a modulated X-ray signal. For these applications the output signal of the X-ray detector is directed through a low band filter means having a cut-off frequency above the modulation frequency and therefrom through a band pass filter means having a center frequency substantially that of the modulation frequency. Both the low band filter means and the band pass filter means may be active filter circuits having gain. The detector and associated circuitry described may be used in conjunction with a servo motor control of a scanning panoramic X-ray unit so as to control the speed of the scan.

BRIEF DESCRIPTION OF THE DRAWINGS

Other objects and advantages of the invention will become apparent upon reading the following detailed description and upon reference to the drawings in which.

DETAILED DESCRIPTION OF THE DRAWINGS

Figure 1:
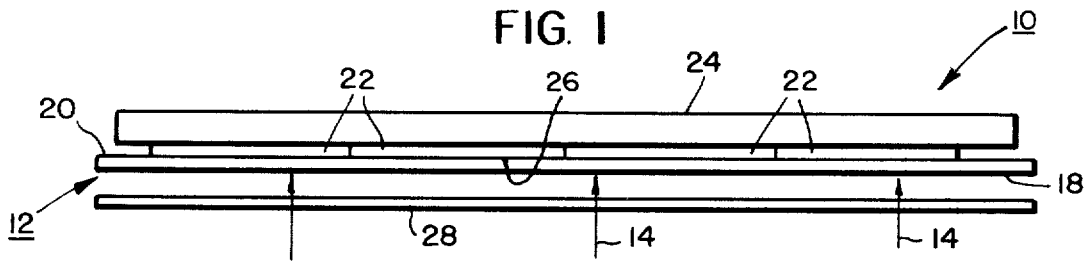
FIG. 1 is a view of the X-ray detector including the invention.
Figure 2:
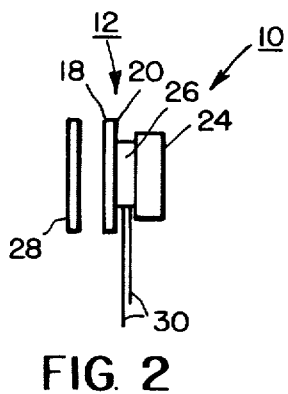
FIG. 2 is another view of the X-ray detector.

FIG. 1 and FIG. 2 are two views of a X-ray detector 10 suitable for practicing the invention and are described concurrently. A fluorescent screen 12 is used to convert incident X-rays 14 into light. The fluorescent screen 12 can have an X-ray transparent base 18, such as for example plastic with a coating 20 of a fluorescent material such as calcium tungstate or other known material which has a property of a emitting light upon excitation by X-rays. It is preferred that the fluorescent material have a short persistance so that the amount of emitted light corresponds to the immediate intensity of the exciting X-ray. Such fluorescent screens are commercially available.

One or more semiconducter photosensitive cells 22 are mounted on a fiberglass board 24 for rigidity. Photovoltaic energy conversion cells are preferable to the photoconductor cells presently available as the geometry and response speed of the former are superior to that of the latter. Conductive epoxy can be use to affix the photovoltaic energy conversion cell 22 to the board 24 and to make electrical contact with printed wiring on the board. A plurality of cells may be used. If more than one photovoltaic energy conversion cell is used, it is preferable to connect them in shunt so as to present the lowest output impedance, an important consideration to avoid generating electrical noise. The cells are preferably those of the silicon type. Silicon type cells have better noise characteristics than selenium type presently available.

The photovoltaic energy conversion cell has an active surface 26 and generates electrical current upon receipt of light upon said active surface 26. In the present invention, the active surface is in optical communication with the fluorescent screen 12. The simplest arrangement is for the active surface to be in proximity to the coated side 20 of the fluorescent screen 12. The photovoltaic energy conversion cell 22 can be selected to have a spectral response corresponding to the optical emission of the fluorescent sceen 12.

An electrostatic shield 28 interposed between the fluorescent screen and the X-ray source. The shield 28 is constructed of conductive material to shield the photovoltaic energy conversion cell 22 from both background electrical noise and ambient light. Copper and aluminum foil have been found to be satisfactory. The foil must be thin enough so as to avoid excessive attenuation or scattering of the incident X-rays. Foil 1 mil. thick performs well. The detector 10 may be retained in a housing for protection.

Figure 3:
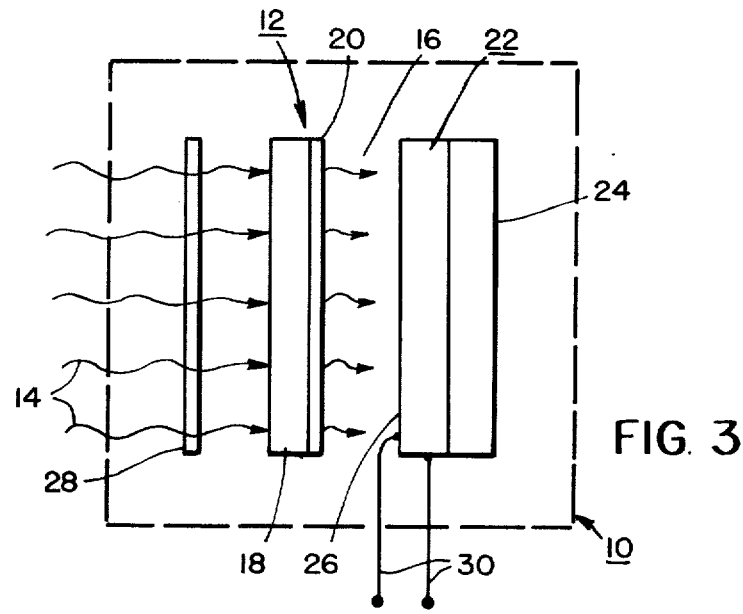
FIG. 3 is an optical diagram of the X-ray detector of FIGS. 1 and 2.

FIG. 3 is an optical diagram for explaining the operation of the X-ray detector including the invention, the elements are as heretofore described. Incoming X-rays 14 pass through the electrostatic shield 28 and excite the fluorescent material 20 which emits light 16. The light is received by the photovoltaic energy conversion cell 22 and converted to electrical energy available at the ouput terminals 30. In the case of a very low impedance load, the output of the photovoltaic conversion cell will be an electrical current corresponding to the magnitude of the detected X-ray.

Important advantages are obtained by the disclosed X-ray detector. The effective area of the detector may be shaped to fit any need. For example, in a panoramic X-ray unit, a rectangular detector is required to intercept the X-ray beam, which is approximately 6 inches in height and one-eighth or one-fourth inches wide at the image recovery area where the detection must take place. This geometry may easily be met with the disclosed apparatus. The thickness of the detector is less than that of the tube detector. An important electrical consideration for low noise application is the low output impedance obtained from silicon cells.

In some applications, the X-ray source is an X-ray tube driven by a high voltage 60-cycle source. The voltage is rectified by a diode bridge circuit or the X-ray tube itself. The tube generates X-rays which have a 120 cycle envelope or a 60 cycle envelope respectively.

Figure 4:
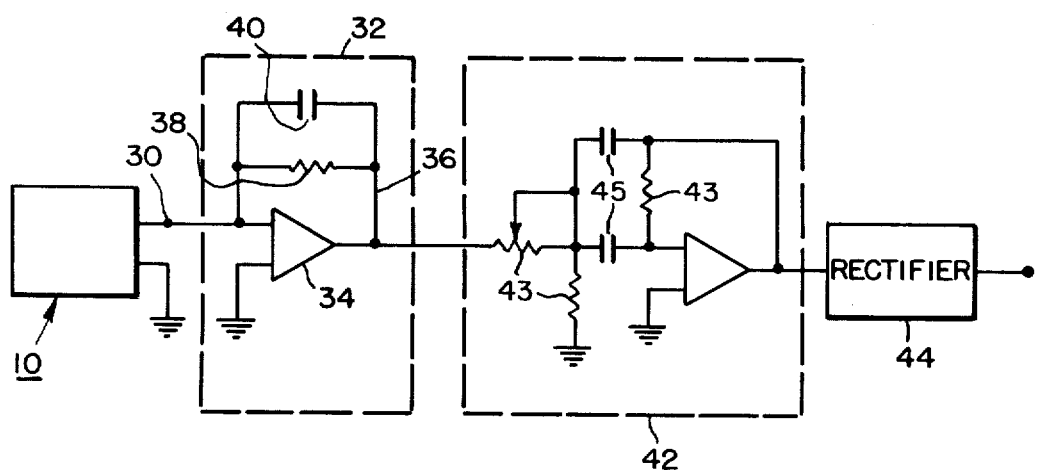
FIG. 4 is a schematic of a signal conditioning circuitry for the output of the X-ray detector of FIG. 1; and, FIG. 5 is a diagram of a panoramic X-ray unit which includes the invention.

FIG. 4 is a block diagram of detector circuitry used for detecting X-rays which energy is contained within such modulation envelopes. The response of the detector must be fast enough to follow the envelope of the X-ray. Upon receipt of a modulated X-ray, the detector responds accordingly with an output signal having an amplitude that is a function of the energy of X-rays received and also being cyclic at the same frequency as that of the envelope. The presence of an alternating component of the output signal is an advantage as it is well known AC amplifiers are more immune to drift than DC amplifiers.

The output of the detector is amplified by DC amplifier 32. The first amplifier has a very low input impedance, appoaching that of a short circuit which causes the detector to behave as a current source. The low impedance across the amplifiers input is a decided advantage in minimizing electrical noise pick up. The first amplifier contains a low noise, operational amplifier 34 that has a feedback network 36 including a resistor 38 and a capacitor 40 in shunt. The feedback network 36 has the effect of reducing the gain at higher frequencies. Therefore, the amplifier acts as an low pass filter having a cut off point chosen to be above the frequency of the detected envelope. This arrangement stablizes the gain of the circuit and further reduces high frequency noise that may have been generated. The output of the first amplifier is an amplified signal the magnitude of which is equal to the resistor 38 times the signal current produced by the photovoltaic energy conversion cell 22 of the detector.

The output signal of the first amplifier 12 is applied across the input of an AC amplifier 42. The second amplifier 42 including resistors 43 and capacitors 45 are arranged so as to act as a band pass filter, the center frequency of which being the same as the frequency of the detected envelope of the modulated X-ray source. The band pass characteristics of the second amplifier eliminates noise outside the pass band, as well as any DC component of the signal as present on the envelope of the received X-ray. A peak rectifier 44 converts the signal into a DC voltage, the magnitude of which is equal to the peak voltage amplitude of the output signal of the detector 10 and is a function of the intensity of the X-rays energy.

Figure 5:
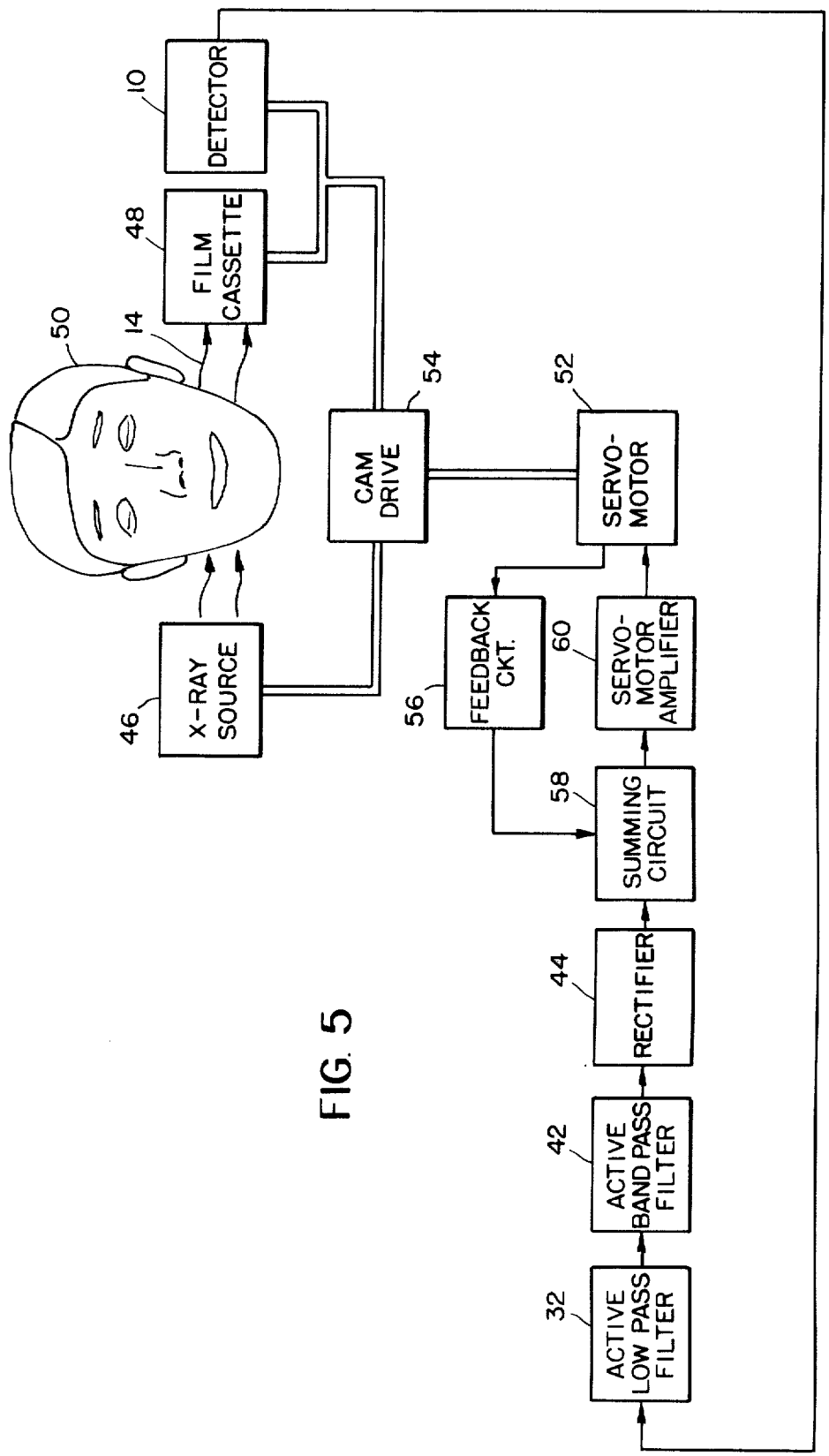

FIG. 5 is a block diagram of a panoramic X-ray unit which includes the present invention. An X-ray source 46 and a film cassette or holder 48 are placed on opposite sides of a patient's skull 50. Both elements 46, 48 rotate about the skull in a predetermined manner keeping a portion of the dental arch in focus. The purpose is to obtain a panoramic or continuous X-ray strip of substantially all the patient's teeth and jaw in one exposure.

As the elements simultaneously rotate, the film strip recording produces in the cassette a continuous X-ray record of the passage around the patient's jaw. The X-rays will be a attenuated by the amount of bone and tissue interposed between the source and the film. When X-raying the patient's front teeth, the X-ray source 46 is behind the patient's neck while the film cassette 48 is in front of the patient's lips resulting in high attenuation of the X-ray beam. In X-raying the patient's side teeth, the X-ray source 46 is on one side of the patient's head and the film cassette 48 is on the other resulting in low attenuation.

X-ray film has only a moderate exposure range. It is therefore, necessary, to alter the amount of exposure on a given amount of film in relation to the portion of the skull being X-rayed. By placing the detector 10 of the invention in proximity of the film cassette 48 a signal may be obtained corresponding to the intensity of the X-ray. This signal is used to control either the intensity of the X-ray source or the speed of the rotating source. In some applications, it is generally undesirable to vary the intensity of the tube, because of the high voltage involved therein and because the    pensation circuitry, used to minimize source line fluctuations, do not generally lend themselves easily to intensity control schemes. It is, therefore, generally preferred to vary the speed of the unit.

In the panoramic X-ray unit of FIG. 5 a variable speed servomotor 52 is used to move both the X-ray source 46 and the corresponding film cassette 48 about the patient's skull by means of a mechanical drive 54. A feedback circuit 56 senses the rotational speed of the servomotor 52 and applies a feedback signal to a summing circuit 58. The output of the detector 10 is amplified by amplifiers 32, 42, rectified by the rectifier circuit of FIG. 4, and applied to summing circuit 58. The difference between the amplitude of the feedback signal and the signal from the rectifier is amplified by a servo amplifier 60 which controls the speed of the servomotor.

When, for instance, the X-ray is looking through the side of the patient's skull where the X-ray attenuation is the lowest the detector output will be at a high level and the speed of the servo-motor will be increased to drive the unit faster thereby reducing exposure time. At the opposite extreme, when X-raying the front teeth, the X-ray beam must pass through the base of the skull and vertibra where attenuation is higher, this produces a lower level from the detector output which causes the servomotor to drive slower resulting in a higher exposure time.

The disclosed X-ray detector may be fabricated to meet any desired geometric configuration. It does not require external high voltage power supplies and is free from undesirable bulk. The X-ray detector may be manufactured for moderate cost. It is rugged and reliable and is suitable for many applications, including application for requirements requiring a low noise X-ray detector. One such application is a panoramic X-ray machine as heretofore described.

We claim:

1. Apparatus for detecting the intensity of X-ray radiation received from an amplitude modulated X-ray source, said apparatus comprising:
   solid state X-ray radiation detection means responsive to X-ray radiation to generate an electrical output signal the magnitude of which is a function of the intensity of the X-ray radiation wherein the response time of said detector means is sufficiently fast enough to follow the changes in X-ray intensity so that said output signal follows the amplitude of the envelope of the modulated X-ray; and
   bandpass filter circuit means for transmitting signals at the modulation frequency while rejecting the signals having frequencies substantially higher and lower than said modulation frequency.

2. Apparatus as defined in claim 1 wherein said detection means has an output impedance of a magnitude so that said detection means approximates a current source.

3. Apparatus as defined in claim 1 wherein said bandpass filter circuit means includes:
   a DC amplifier with low pass filter means feedback;
   a AC amplifier with band pass filter means feedback, said DC amplifier having an input being connected to the detection means and an output connected to said AC amplifier.

4. In combination with an X-ray scanning system, wherein a modulated X-ray radiation source and an X-ray receiving means are moved by variable speed drive, a control system for controlling the rate at which the source and the receiver are moved as a function of the intensity of the X-ray radiation received which comprises:
   an X-ray detection means responsive to X-ray radiation to generate output signal the magnitude of which is a function of the intensity of the X-ray radiation;
   feedback circuit means for providing a feedback signal that is a function of the rate at which said source and receiver are moved;
   comparing means for comparing the feedback signal to the X-ray detector signal for providing a control signal for changing the rate at which said source and said receiver are to be moved; and
   control circuit means for applying the control signal to said variable speed drive in relation to said control signal which corresponds to the intensity of the detected X-ray radiation.

5. In combination with an X-ray scanning system having a X-ray radiation source and an X-ray receiving means movable about a target, a control system for controlling the dosage of X-ray radiation in response to the intensity of X-ray radiation received, which comprises:
   an X-ray detector in proximity to said receiving means for generating an output signal representative of the intensity of the X-ray radiation received; and
   control means responsive to said output signal for adjusting the dosage accordingly during the excursion of said source and receiving means about said target.

6. A control system as set forth in claim 5 wherein said control means varies the speed at which said radiation source and receiving means are moved about the target, thereby adjusting the X-ray dosage.

* * * * *